(12) United States Patent
Fay

(10) Patent No.: US 11,980,561 B2
(45) Date of Patent: May 14, 2024

(54) VERSATILE ARTICULATED DYNAMIC RESPONSE ANKLE FOOT ORTHOSIS

(71) Applicant: United States of America as represented by the Department of Defense, Silver Spring, MD (US)

(72) Inventor: Jeffrey G Fay, Silver Spring, MD (US)

(73) Assignee: UNITED STATES OF AMERICA AS REPRESENTED BY THE SECRETARY OF DEFENSE, Bethesda, MD (US)

( * ) Notice: Subject to any disclaimer, the term of this patent is extended or adjusted under 35 U.S.C. 154(b) by 998 days.

(21) Appl. No.: 15/484,672

(22) Filed: Apr. 11, 2017

(65) Prior Publication Data
US 2017/0296372 A1    Oct. 19, 2017

Related U.S. Application Data

(60) Provisional application No. 62/322,659, filed on Apr. 14, 2016.

(51) Int. Cl.
*A61F 5/01*    (2006.01)

(52) U.S. Cl.
CPC .... *A61F 5/0127* (2013.01); *A61F 2005/0137* (2013.01); *A61F 2005/0167* (2013.01)

(58) Field of Classification Search
CPC ...... A61F 2005/0137; A61F 2005/0167; A61F 5/0127; A61F 5/0102; A61F 5/0585; A61F 5/0111; A61F 5/0113
USPC ..................... 602/5, 23, 27, 28, 29; 128/882
See application file for complete search history.

(56) References Cited

U.S. PATENT DOCUMENTS

| 4,771,768 | A | * | 9/1988 | Crispin | A61F 5/0127 D24/190 |
| 4,791,916 | A | * | 12/1988 | Paez | A61F 5/0123 602/26 |
| 4,934,355 | A | | 6/1990 | Porcelli | |
| 5,086,760 | A | | 2/1992 | Neumann et al. | |
| 5,088,479 | A | | 2/1992 | Detoro | |

(Continued)

FOREIGN PATENT DOCUMENTS

WO    2013158221 A1    10/2013

OTHER PUBLICATIONS

Collins, et al. Nature, Jun. 11, 2015; 522(7555): 212-215. doi: 10.1038/nature14288, published online Apr. 1, 2015.

(Continued)

*Primary Examiner* — Caitlin A Carreiro
(74) *Attorney, Agent, or Firm* — Ning Yang; Anthony Vu

(57) ABSTRACT

An orthotic device including a plurality of posterior dynamic struts and an adjustable posterior multiple strut engager, wherein the plurality of posterior dynamic struts has a first posterior dynamic strut and one or more additional posterior dynamic struts, and wherein the adjustable posterior multiple strut engager is affixed to the first posterior dynamic strut and is adapted to restrain the movement of said one or more additional posterior dynamic struts, and wherein the adjustable posterior multiple strut engager may be adjusted to engage said one or more additional posterior dynamic struts in combination with the first posterior dynamic strut, thereby forming a single posterior dynamic strut assembly of greater rigidity than the first posterior dynamic strut alone.

38 Claims, 16 Drawing Sheets

(56) References Cited

U.S. PATENT DOCUMENTS

| | | | |
|---|---|---|---|
| 5,224,925 A * | 7/1993 | Varn | A61F 5/0585 |
| | | | 602/23 |
| 5,431,624 A | 7/1995 | Saxton et al. | |
| 5,486,157 A | 1/1996 | DiBenedetto | |
| 5,496,263 A | 3/1996 | Fuller, II et al. | |
| 5,542,774 A | 8/1996 | Hoy | |
| 5,593,383 A | 1/1997 | Detoro | |
| 5,611,773 A | 3/1997 | Nash et al. | |
| 5,891,071 A * | 4/1999 | Stearns | A61F 5/0123 |
| | | | 602/26 |
| 5,908,398 A | 6/1999 | Detoro | |
| 5,944,679 A | 8/1999 | Detoro | |
| 6,010,474 A | 1/2000 | Wycoki | |
| 6,409,695 B1 | 6/2002 | Connelly | |
| 6,517,505 B1 * | 2/2003 | Veldman | A61F 5/0111 |
| | | | 602/5 |
| 7,112,180 B2 * | 9/2006 | Guenther | A61F 5/0111 |
| | | | 602/29 |
| 7,462,160 B2 * | 12/2008 | Nobbe | A61F 5/0113 |
| | | | 602/5 |
| 7,513,880 B2 * | 4/2009 | Ingimundarson | A43B 13/12 |
| | | | 602/23 |
| 7,569,022 B2 | 8/2009 | Morinaka | |
| 8,740,829 B2 | 6/2014 | Lee et al. | |
| 8,998,834 B2 | 4/2015 | Phillips | |
| 9,186,270 B2 | 11/2015 | Blanck | |
| 9,433,522 B2 | 9/2016 | Bader | |
| 2006/0276736 A1 | 12/2006 | Devreese | |
| 2007/0027421 A1 | 2/2007 | Nobbe et al. | |
| 2012/0271214 A1 | 10/2012 | Blanck | |
| 2013/0046218 A1 | 2/2013 | Wiggin et al. | |
| 2013/0053738 A1 * | 2/2013 | Kandt | A61F 5/0123 |
| | | | 602/6 |
| 2013/0165833 A1 | 6/2013 | Blanck | |
| 2013/0281898 A1 | 10/2013 | Cropper et al. | |
| 2013/0338795 A1 | 12/2013 | Townsend et al. | |
| 2014/0257158 A1 | 9/2014 | Lee et al. | |

OTHER PUBLICATIONS

Malcolm, et al. (2013) PLoS ONE 8(2): e56137. doi:10.1371/journal.pone.0056137, published online Feb. 13, 2013.

Banziger et al., Journal of the Association of Children's Prosthetic-Orthotic Clinics 1991; vol. 26, No. 2, p. 65.

Lawrence et al., J. Prosthet. Orthot. 2006; 18:68-71.

Nobbe Orthopedics, Inc., "New Products The DROCS system"; 2012; http://www.nobbeorthopedics.com/np-drocs.htm; Dec. 17, 2015.

* cited by examiner

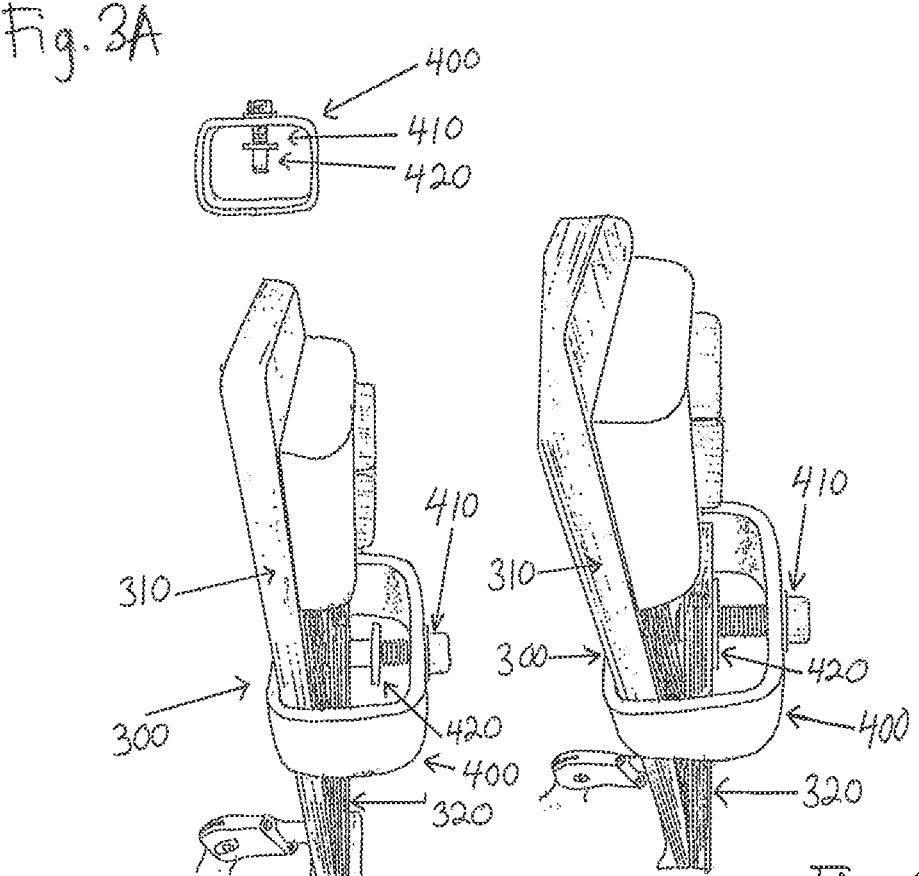

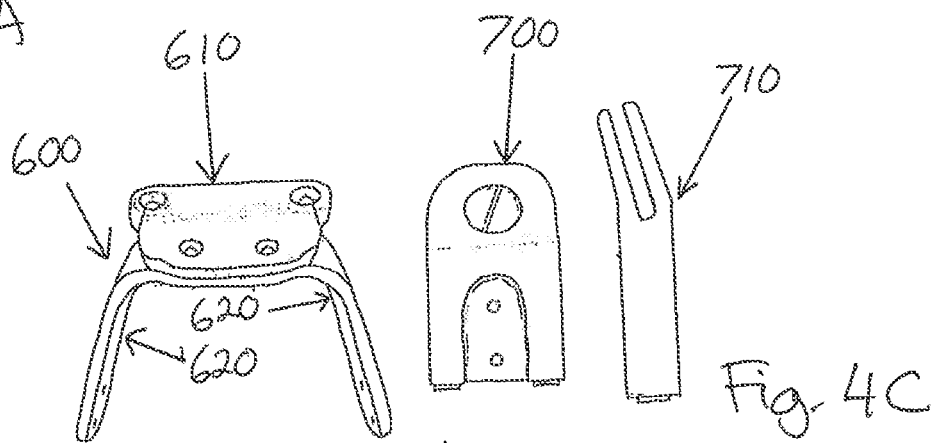
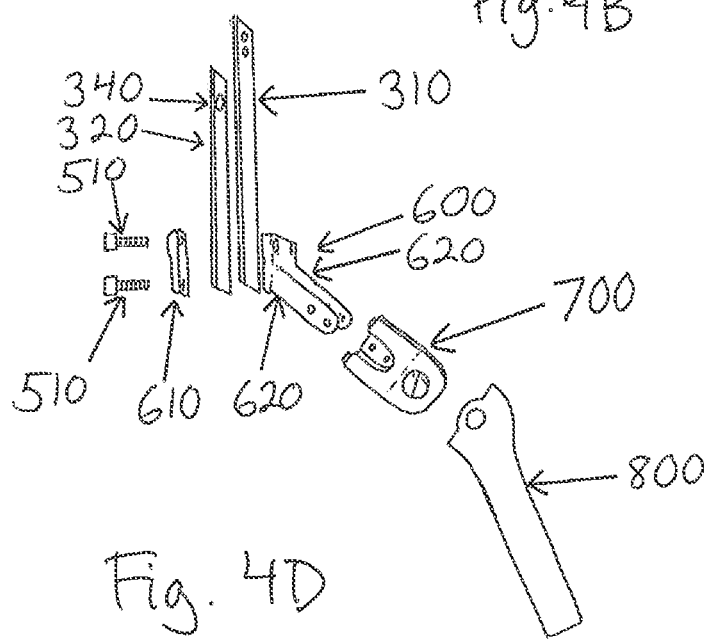

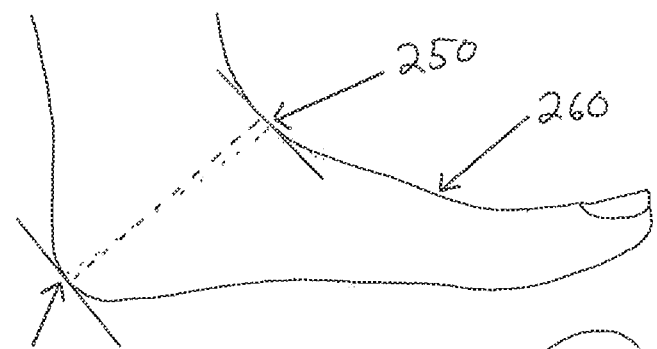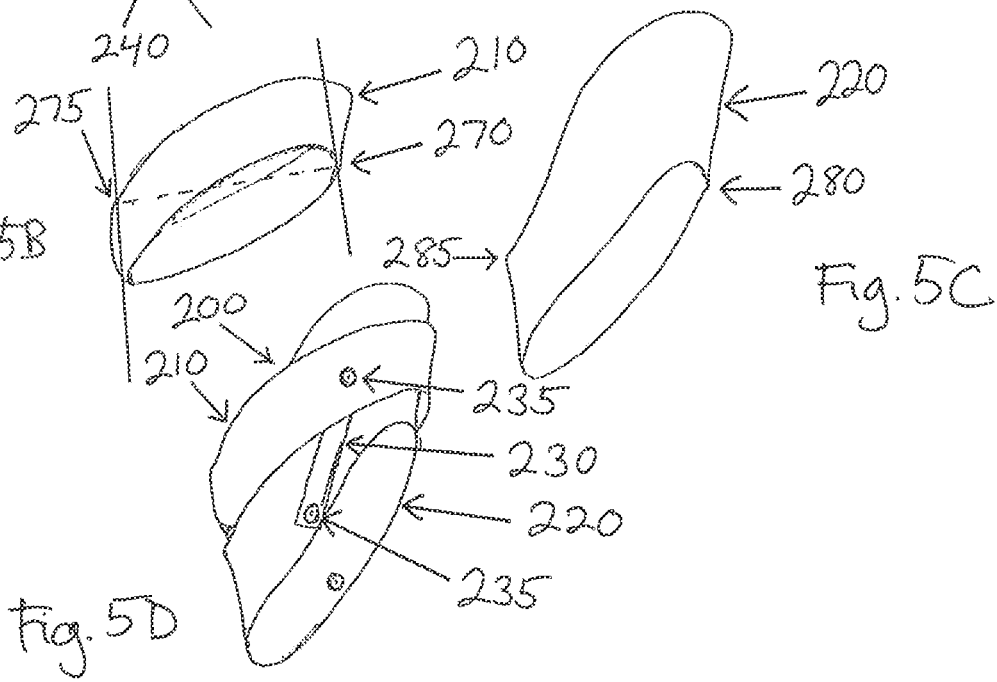

VERSATILE ARTICULATED DYNAMIC RESPONSE ANKLE FOOT ORTHOSIS

CROSS REFERENCE TO RELATED APPLICATIONS

The present application claims the benefit of U.S. Provisional Patent Application No. 62/322,659 filed Apr. 14, 2016 the entire contents of which is incorporated by reference herein.

FIELD OF THE INVENTION

The subject matter of the instant invention relates to an orthotic device designed for patients with lower limb motor dysfunction, including patients with functional deficiencies in the calf due to triceps surae weakness.

BACKGROUND OF INVENTION

Numerous ankle foot orthotic devices (AFOs) are commercially available in a variety of designs. While providing some benefit to patients suffering from leg injuries of various etiologies, commercially available devices are also limited in various respects. Many AFOs provide limb support by locking the ankle of the wearer in place. Typically, in such devices compensatory and abnormal gait patterns are still present in the wearer; a normal walking gait, running or other high impact gait, are not achieved.

While an AFO with a non-articulated ankle may be necessary for some patients, for other patients the physical limitations associated with such devices may be unnecessarily restrictive. For example, during the process of evaluating, casting, and fitting of their orthoses, many patients with motor dysfunction of their lower limb(s), including involving their triceps surae, present with decent ankle range of motion (ROM), with pain limited to particular arcs within their available ROM, e.g., pain only presents as the patient's foot/ankle moves into dorsiflexion late in stance. Thus, such patients may benefit greatly from an orthotic device which permits greater ankle ROM than provided by conventional devices. Indeed, the use of conventional non-articulating AFOs by these patients may cause unwarranted atrophy of calf muscles as well as needless progressive soreness and overall tightness of the foot/ankle as a result of being held in a strict position for a period of time.

In contrast, if possible, use of an orthotic device which permits greater ankle ROM can provide advantages for many patients. These benefits include, e.g., preserving normal physiological and biomechanical benefits associated with maintaining the normal secretion of synovial fluid and glycosaminoglycan production which are important for joint health and shock absorption within the joint space and articular cartilage; permitting functional shock absorption and knee stability by allowing plantarflexion motion in early stance; and providing a more seamless transition throughout the gait cycle without conscious interruption.

Thus, notwithstanding the benefits of existing orthotic devices, there currently remains a need for improved orthotic devices, particularly those which provide ankle ROM and free plantarflexion, but which resist dorsiflexion where pain or functional deficit exists. In particular, devices for use by patients with motor dysfunction of their lower limb(s) but who still possess sufficient ankle ROM for walking and other gaits and activities with higher impact are needed.

SUMMARY OF THE INVENTION

In a first aspect, the invention relates to an orthotic device comprising a plurality of posterior dynamic struts and a posterior multiple strut engager, wherein the plurality of posterior dynamic struts comprises a first posterior dynamic strut and one or more additional posterior dynamic struts, and wherein the posterior multiple strut engager is affixed to the first posterior dynamic strut and is adapted to restrain the movement of said one or more additional posterior dynamic struts, and wherein the posterior multiple strut engager may be adjusted to engage said one or more additional posterior dynamic struts in combination with the first posterior dynamic strut, thereby forming a single posterior dynamic strut assembly of greater rigidity than the first posterior dynamic strut alone. In one embodiment, the plurality of posterior dynamic struts comprises a material that allows a dynamic response in the device. In a particular embodiment, the material is selected from the group consisting of stainless steel, carbon, carbon fiber, titanium, fiberglass, resin, plastic, KEVLAR, aluminum, and composites thereof. In a particular embodiment, the material comprises carbon fiber.

In another embodiment, the posterior multiple strut engager comprises a fastener selected from the group consisting of screws, clips, clamps, straps, springs, nuts, bolts, and a combination thereof. In a particular embodiment, the fastener comprises a screw clamp. In another embodiment, the fastener comprises a screw clamp and a nut.

In another embodiment, the aforementioned orthotic device further comprises a proximal cuff, distal mechanical ankle joints, and a distal footplate. In a particular embodiment, the plurality of posterior dynamic struts are attached at their distal ends to the distal mechanical ankle joints and the first posterior dynamic strut is attached at its proximal end to the proximal cuff, and wherein the distal mechanical ankle joints are attached medially and laterally to the distal footplate. In a particular embodiment, the distal mechanical ankle joints are double action ankle joints. In another embodiment, the distal mechanical ankle joints are contoured double action ankle joints.

In another embodiment, the proximal cuff comprises an inner static cuff component and an outer dynamic cuff component. In a particular embodiment, the outer dynamic cuff component is connected to the inner static cuff component such that the outer dynamic cuff component can slidably translate over the inner static cuff component during use. In an additional embodiment, the inner static cuff component comprises a material selected from the group consisting of thermoplastics, carbon fiber, nylon or composites thereof. In a particular embodiment, the material is a copolymer of thermoplastic materials. In another embodiment, the outer dynamic cuff component comprises a material that allows a dynamic response in the cuff. In a particular embodiment, the material is selected from the group consisting of stainless steel, carbon, carbon fiber, titanium, fiberglass, resin, plastic, KEVLAR, aluminum, and composites thereof. In a particular embodiment, the outer dynamic cuff component comprises a carbon fiber material.

In another embodiment, the distal medial and lateral mechanical ankle joints in the orthotic device are angled from about 25 to about 35 degrees from a straight line bisecting a patient's model's base of heel and forefoot with respect to talocrural ankle axis. In a particular embodiment, the angle depends upon a specific patient presentation. In a particular embodiment, the angle is about 30 degrees.

In another embodiment, the distal footplate comprises a heel cup. In a particular embodiment, the heel cup comprises a thermoplastic material.

In an additional embodiment, the aforementioned orthotic device may further comprise a bridging piece. In a particular embodiment, the plurality of posterior dynamic struts is attached at their distal ends to the distal medial and lateral mechanical ankle joints via the bridging piece. In a particular embodiment, the plurality of posterior dynamic struts are attached at their distal ends to the distal medial and lateral mechanical ankle joints by sandwiching the distal ends of said plurality of posterior dynamic struts between the bridging piece and a corresponding faceplate of the bridging piece. In a particular embodiment, the corresponding faceplate of the bridging piece is removable and central to the bridging piece. In a particular embodiment, the bridging piece in the device is angled from about 0-15 degrees from a perpendicular line bisecting a line formed by bisecting a patient model's base of heel and forefoot with respect to talocrural ankle axis. In another particular embodiment, the angle is about 8 degrees.

In another embodiment, the foregoing orthotic device further comprises joint stirrups. In a particular embodiment, the joint stirrups are double action joint stirrups. In a particular embodiment, the distal medial and lateral mechanical ankle joints are attached to the footplate via the joint stirrups. In one embodiment, the joint stirrups in the device are angled from about 25-35 degrees with respect to talocrural ankle axis. In a particular embodiment, the angle is about 30 degrees.

In another aspect, the invention relates to a method of assisting a patient with a motor dysfunction of a lower limb comprising fitting the patient with the orthotic device of the instant invention; placing the orthotic device on the lower limb of the patient; and adjusting the posterior multiple strut engager of the orthotic device such that only the first posterior dynamic strut is engaged in the orthotic device, thereby providing sufficient strut rigidity in the orthotic device to assist the patient with walking. In a particular embodiment, the method further comprises modifying the orthotic device to remove any additional posterior struts which are not engaged in the orthotic device and/or removing the multiple strut engager from the orthotic device.

In another aspect, the invention relates to a method of assisting a patient with a motor dysfunction of a lower limb comprising fitting the patient with the orthotic device of the instant invention; placing the orthotic device on the lower limb of the patient; and adjusting the posterior multiple strut engager of the orthotic device such that at least one of the one or more additional posterior dynamic struts are combined with the first posterior dynamic strut, thereby forming a single posterior dynamic strut assembly of greater rigidity than the first posterior dynamic strut alone, and thereby providing sufficient rigidity in the orthotic device to assist the patient with running or other high impact activity. In a particular embodiment, one of said one or more additional posterior dynamic struts is combined with the first posterior dynamic strut. In another particular embodiment, two or more of said one or more additional posterior dynamic struts are combined with the first posterior dynamic strut.

In particular embodiments of the aforementioned aspects, the motor dysfunction is a functional deficiency due to triceps surae weakness.

In additional embodiments of the methods of the instant invention, the posterior multiple strut engager is adjusted by the patient. In a particular embodiment, the posterior multiple strut engager is adjusted by the patient during use, thereby providing a desired amount of strut rigidity in the device necessary for a desired gait.

In another aspect, the invention relates to an orthotic device comprising: a proximal calf cuff; first and second posterior dynamic struts; a proximal posterior multiple strut engager; a bridging piece; distal medial and lateral contoured mechanical double action ankle joints; distal double action joint stirrups; and a distal footplate; wherein the first posterior dynamic strut is attached at a proximal end to the proximal calf cuff; and wherein the first and the second posterior dynamic struts are approximately vertically stacked; and wherein the distal ends of said first and said second posterior dynamic struts are attached to the bridging piece; wherein the distal ends of said first and said second posterior dynamic struts are attached to the proximal ends of the distal medial and lateral contoured mechanical double action ankle joints via the bridging piece; wherein the distal ends of the distal medial and lateral contoured mechanical double action ankle joints are attached to the proximal ends of the distal double action joint stirrups; wherein the distal ends of the distal double action joint stirrups are attached to the underside of the distal footplate; wherein the proximal posterior multiple strut engager is mounted on the anterior proximal end of the first posterior dynamic strut and wherein said proximal posterior multiple strut engager may be adjusted to engage either the first posterior dynamic strut alone, or may be adjusted to engage the first posterior dynamic strut in combination with the second posterior dynamic strut, thereby forming a posterior dynamic strut assembly of greater rigidity than the first posterior dynamic strut alone.

In another aspect, the invention relates to an orthotic device which comprises a proximal cuff which comprises an inner static cuff component and an outer dynamic cuff component. In a particular embodiment, the outer dynamic cuff component is connected to the inner static cuff component such that the outer dynamic cuff component can slidably translate over the inner static cuff component during use, thereby reducing friction against the wearer's skin during use of the device. In an additional embodiment, the inner static cuff component may comprise a material selected from the group consisting of thermoplastics, carbon fiber, nylon or composites thereof. In a particular embodiment, the material is a copolymer of thermoplastic materials. In another embodiment, the outer dynamic cuff component may comprise a material that allows a dynamic response in the cuff. In a particular embodiment, the material is selected from the group consisting of stainless steel, carbon, carbon fiber, titanium, fiberglass, resin, plastic, KEVLAR, aluminum, and composites thereof. In a particular embodiment, the outer dynamic cuff component comprises a carbon fiber material.

BRIEF DESCRIPTION OF THE DRAWINGS

FIG. 2A depicts "initial contact"; FIG. 2B depicts the "loading response" phase; FIG. 2C depicts the early part of the "mid-stance" phase; FIG. 2D depicts the later part of the "mid-stance" phase; FIG. 2E depicts the "terminal stance" phase; FIG. 2F depicts the "pre-swing" phase of gait.

FIGS. 3A-3C depicts detailed views of an embodiment of the instant invention which comprises a screw clamp (FIG.

3A) as a multistrut engager, and specifically the use of a nut and screw clamp in combination to control the engagement of a secondary posterior dynamic strut with a primary posterior dynamic strut in the device (FIG. 3B and FIG. 3C). FIG. 3B and FIG. 3C depict different rotations of the nut 420 on the screw 410 to change the location along the shaft of the screw 410.

FIGS. 4A-4D depict component parts of an embodiment of the instant invention, including bridging piece (FIG. 4A); joint (FIG. 4B); joint (side view) (FIG. 4C); and additional component parts as labeled in the text (FIG. 4D).

FIGS. 5A-5D illustrate details regarding measuring a wearer's ankle for customizing the fit of a proximal cuff according to an embodiment of the device of the instant invention. The dotted line in FIG. 5A depicts a perpendicular distance between the point at the apex of the heel curve 240 and the apex on the dorsum side of the foot 250 of the patient used to determine the appropriate opening dimension from the anterior-distal trimline 270 to the posterior-superior trimline 275 of the inner static calf cuff (FIG. 5B), and from the anterior-distal trimline 280 to the posterior-superior trimline 285 of the outer dynamic calf cuffs (FIG. 5C). As explained in the text, the inner static calf cuff 220 dimension can be greater than the actual measurement, but the outer dynamic calf cuff 210 dimension depicted in FIG. 5B should closely approximate the actual measurement taken on the patient; the closer to the actual measurement, the less the posterior portion of the outer dynamic calf cuff 210 is angled inferiorly relative to the anterior portion of the calf cuffs 200 (depicted in FIG. 5D).

DETAILED DESCRIPTION

Figure 1:
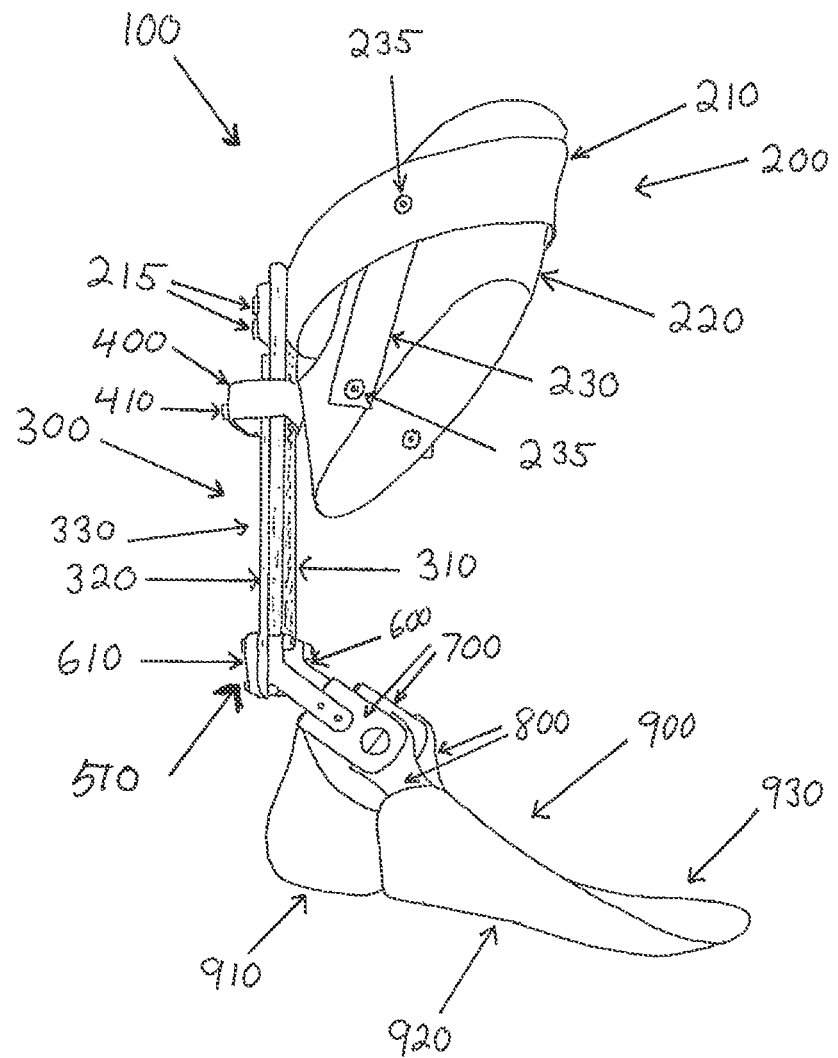
FIG. 1 depicts a side view of an embodiment of an orthotic device of the instant invention.

While the specification concludes with the claims particularly pointing out and distinctly claiming the invention, it is believed that the present invention will be better understood from the following description.

The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include components in addition to those recited in the claim, but only if the additional components do not materially alter the basic and novel characteristics of the claimed invention.

All ranges recited herein include the endpoints, including those that recite a range "between" two values. Terms such as "about," "generally," "substantially," "approximately" and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value. Unless otherwise indicated, as used herein, "a" and "an" include the plural, such that, e.g., "a strut" can mean at least one strut, as well as a plurality of struts, i.e., more than one strut.

Where used herein, the term "and/or" when used in a list of two or more items means that any one of the listed characteristics can be present, or any combination of two or more of the listed characteristics can be present. For example, if an orthotic device of the instant invention is described as containing characteristics A, B, and/or C, the device can contain A feature alone; B alone; C alone; A and B in combination; A and C in combination; B and C in combination; or A, B, and C in combination. The entire teachings of any patents, patent applications or other publications referred to herein are incorporated by reference herein as if fully set forth herein.

The term "proximal" as used herein refers to a location situated next to or near the point of attachment or origin or a central point, or located toward the center of the body. The term "distal" as used herein refers to a location that is situated away from the point of attachment or origin or a central point, or located away from the center of the body. The term "anterior" refers to a location that is ahead of or to the front of another location. The term "posterior" refers to a location that is behind or to the rear of another location.

As used herein, the term "rigid" is intended to denote that an element of the device is generally devoid of flexibility. For example, components of the device of the instant invention that are "rigid," do not lose their overall shape when force is applied. Components that are "semi-rigid" have some degree of flexibility or resiliency. As used herein, "sufficient rigidity" of one or more struts for a particular gait may be determined by one of skill in the art without undue experimentation.

As used herein, the term "flexible" refers to components of the device that may be bent or deform when force is applied.

One of skill in the art will appreciate that a proper gait cycle is made up of an initial "stance phase" which is the weight bearing portion of the gait cycle (i.e., the period of direct contact of the foot against the ground), and a "swing phase" which is the non-weight bearing portion of the gait cycle (i.e., the period in which the foot swings above the ground, from toe-off to subsequent heel strike). The triceps surae act to control the tibial progression during the stance phase of the gait cycle. As the body vector moves anterior through the foot and passes the ankle joint, the requirement for triceps surae engagement increases to stabilize foot/ankle/knee complex.

The invention relates to an orthotic device comprising multiple dynamic posterior struts, wherein said device allows a patient with motor dysfunction of a lower limb to experience not only a more natural movement of a lower extremity throughout a proper walking gait cycle, but also permits a more normal gait during activities with higher impact, such as running, by allowing free plantarflexion in early stance and preswing, and by resisting dorsiflexion eccentrically in mid to late stance. Particularly, the orthotic device of the instant invention comprises a plurality of posterior dynamic struts ("struts") which comprises a first posterior dynamic strut and one or more additional posterior dynamic struts. As understood herein, the "first" posterior dynamic strut also may be referred to herein as a "primary" strut; the "one or more additional posterior dynamic struts" may also be referred to herein as "secondary" struts. It is contemplated herein that the term "secondary" can encompass one or more additional struts, e.g., a posterior dynamic strut assembly may comprise two posterior dynamic struts (i.e., one primary strut in combination with one secondary strut); or an assembly may comprise three or more posterior dynamic struts (i.e., one primary strut in combination with two or more secondary struts.)

As contemplated herein, the posterior dynamic struts of the instant invention may be "stacked" or otherwise arranged "back to front" such that the posterior face of a first (primary) strut is in contact (or nearly in contact) with the anterior face of a second posterior (secondary) strut. Similarly, a third strut may be stacked with the first two struts by combining the posterior face of the secondary strut with the anterior face of yet another secondary strut. In this manner, a plurality of struts may be stacked in the orthotic device of the instant invention, i.e., arranged in an orientation from back to front and approximately vertically, i.e., in "piggyback" fashion, in the device.

As used herein, the term "triceps surae" encompasses muscles of the calf, including the gastrocnemius and soleus muscles, located in the posterior of the human leg. Thus, as understood herein, a patient with "a motor dysfunction of a lower limb", a "lower limb" or "calf" injury, a "functional deficiency due to triceps surae weakness" and like terms includes, but is not limited to, individuals who may have a functional deficit comprising the gastrocnemius muscle and/ or the soleus muscle in one or more legs.

The present invention relates to an orthotic device designed to support the ankle and foot of a patient (AFO). In particular, the AFO of the instant invention is designed for patients with motor dysfunction of a lower limb(s), including patients with functional deficiencies due to triceps surae weakness. More particularly, the invention relates to an AFO which allows the patient to experience not only a more natural movement of a lower extremity throughout a proper walking gait cycle, but also permits a more normal gait during activities with higher impact, such as running, by allowing free plantarflexion in early stance and preswing, the arc of motion that is typically free of pain in patients with functional deficiencies due to triceps surae weakness, and by resisting dorsiflexion eccentrically in mid to late stance, the arc of motion that is typically painful, or functionally deficient in such patients.

The orthotic device of the instant invention is designed for patients with lower limb injuries but who retain a range of motion in the ankle such that a conventional brace which provides support by locking the ankle is not clinically necessary. Such patients include individuals with soft tissue injuries and/or perineal nerve injuries ("drop foot") who need a device to assist leg swing.

In a particular embodiment, the orthotic device of the instant invention is an articulated dynamic ankle foot orthosis, i.e., an orthotic device that provides support and also assists with the initiation and performance of movement of the ankle. In a particular embodiment, it is contemplated herein that the device of the instant invention can provide a clinical benefit to patients with triceps surae weakness as the device is designed to allow free plantarflexion in early stance and preswing (arc of motion that is typically free of pain in these patients) and to resist dorsiflexion eccentrically in mid to late stance (arc of motion that is typically painful, or functionally deficient in these patients) i.e., it is contemplated herein that the device of the instant invention is designed to recreate functions of the calf muscle. Thus, as contemplated herein, when the patient is walking, the AFO of the instant invention will permit the patient to plantarflex their foot when a force moment passes posterior to the talocrural (ankle) joint such as when the patient makes heel contact. As the force moments pass anterior to the ankle joint, the posterior dynamic struts (primary and secondary) in the device will resist dorsiflexion of the ankle and absorb energy by flexion of the struts. As the force moments anterior to the ankle reduce, energy absorbed by the flexed struts will be returned by extension of the struts with momentum transferred through the ankle joint allowing the foot to plantarflex. This is depicted in FIGS. 2A-2F and discussed in greater detail below.

Additional advantages provided by the device of the instant invention include the ability of the wearer to adjust the multiple strut engager wherever desired. For example, in an embodiment of the invention comprising a strut engager which comprises a fastener comprising a screw clamp and nut assembly described in detail herein, the patient has the ability to adjust the nut within the engager to cause the secondary strut to flex sooner or later creating greater or less resistance of the system. For example, if the patient desired to run, they may not feel a great enough resistance to the higher impact forces generated immediately after when their foot contacts the ground. Accordingly, the patient can tighten the nut within the engager to make contact with the secondary strut so that both struts flex at the same time, thus eliminating the lag time between the first and second strut flexion. The patient could also loosen the nut within the engager to delay the flexion of the secondary strut. This may be useful, for example, when the patient is walking up hills so the patient doesn't feel a tremendous amount of resistance to roll over the third (forefoot) rocker.

Thus, in a first aspect, the invention relates to an orthotic device comprising a plurality of posterior dynamic struts and a posterior multiple strut engager, wherein the plurality of posterior dynamic struts comprises a first posterior dynamic strut and one or more additional posterior dynamic struts, and wherein the posterior multiple strut engager is affixed to the first posterior dynamic strut and is adapted to restrain the movement of said one or more additional posterior dynamic struts, and wherein the posterior multiple strut engager may be adjusted to engage said one or more additional posterior dynamic struts in combination with the first posterior dynamic strut, thereby forming a single posterior dynamic strut assembly of greater rigidity than the first posterior dynamic strut alone.

Referring to the drawings, a particular embodiment of the invention is depicted in FIG. 1. As depicted, an orthotic device of the instant invention 100 ("device") comprises a proximal calf cuff 200; outer dynamic calf cuff component 210; static calf cuff component 220; flexible strapping 230; rivets 235; screws 215; posterior struts 300 including first 310 and second 320 posterior dynamic struts; a posterior dynamic strut assembly 330; a proximal posterior multiple strut engager 400; screw 410 threaded into the posterior portion of the engager 400; (strut engager nut not visible); bolts 510; a bridging piece 600; faceplate 610; distal medial and lateral mechanical double action ankle joints 700; distal double action joint stirrups 800; and a distal footplate 900; heel cup 910; underside 920 of the distal footplate 900; and forefoot 930; wherein the first posterior dynamic strut 310 is attached at a proximal end to the proximal calf cuff 200; and wherein the first 310 and the second 320 posterior dynamic struts are approximately vertically stacked; and wherein the distal ends of said first 310 and said second 320 posterior dynamic struts are attached to the bridging piece 600; wherein the distal ends of said first 310 and said second 320 posterior dynamic struts are attached to the proximal ends of the distal medial and lateral mechanical double action ankle joints 700 via the bridging piece 600; wherein the distal ends of the distal medial and lateral mechanical double action ankle joints 700 are attached to the proximal ends of the distal double action joint stirrups 800; wherein the distal ends of the distal double action joint stirrups 800 are attached within and on the underside 920 of the distal footplate 900 (shown in detail by dashed lines in FIG. 7); wherein the proximal posterior multiple strut engager 400 is mounted on the anterior proximal end of the first posterior dynamic strut 310 and wherein said proximal posterior multiple strut engager 400 may be adjusted to engage either the first posterior dynamic strut 310 alone, or may be adjusted to engage the first posterior dynamic strut 310 in combination with the second posterior dynamic strut 320, thereby forming a posterior dynamic strut assembly 330 of greater rigidity than the first posterior dynamic strut alone. In this particular embodiment, the joints may be contoured double action ankle joints.

Figure 2A:
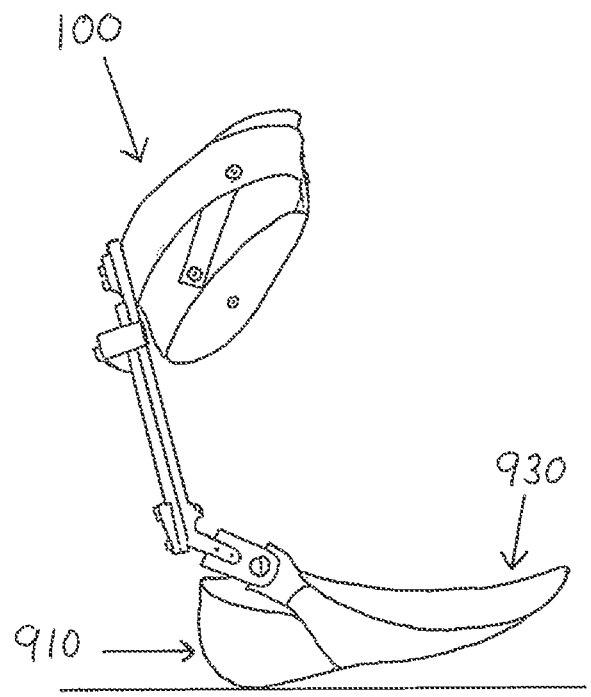
FIGS. 2A-2F depict the different sequential stance phases of a typical walking gait cycle according to an embodiment of the instant invention.

FIGS. 2A-2F depict the different sequential stance phases of a typical walking gait cycle according to an embodiment of the instant invention. Specifically, FIG. 2A depicts the "initial contact" of a user wearing an embodiment of the device of the instant invention 100. As depicted, desirably, the heel cup 910 makes the first contact with the ground. The ankle is typically considered to be in a neutral position or at 90 degrees with only the heel cup 910 contacting the ground and the forefoot 930 still in the air.

Figure 2B:
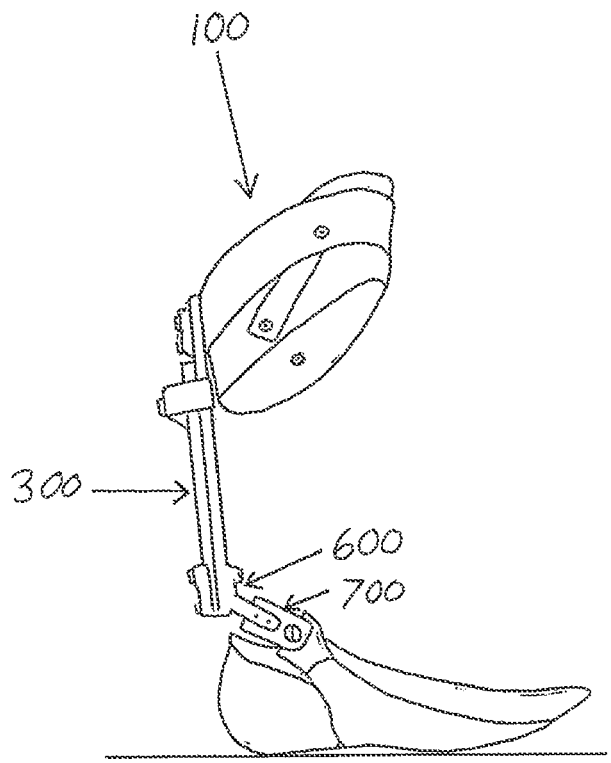

FIG. 2B depicts the "loading response" phase which includes the first of three rockers, also known as the heel rocker. In the embodiment of the device of the instant invention 100 depicted, the ankle is allowed to naturally plantarflex and is not impeded by the posterior strut(s) 300 because of the connection of the strut(s) to the mechanical ankle joints 700 by way of the bridging piece 600. It is believed that the ability for the patient to plantarflex their ankle within the device is unique to the instant invention. As depicted, the ankle plantarflexes about 10 degrees and the forefoot makes contact with the ground by the end of this phase. Notably, as contemplated herein, the inferior joint channel of the ankle joint 700 can either have a spring installed or nothing within the channel to allow motion to take place. In contrast, prior art devices with posterior calf dynamic struts and which desire to eliminate plantarflexion of the ankle and AFO commonly include a pin in the inferior channel.

Figure 2C:
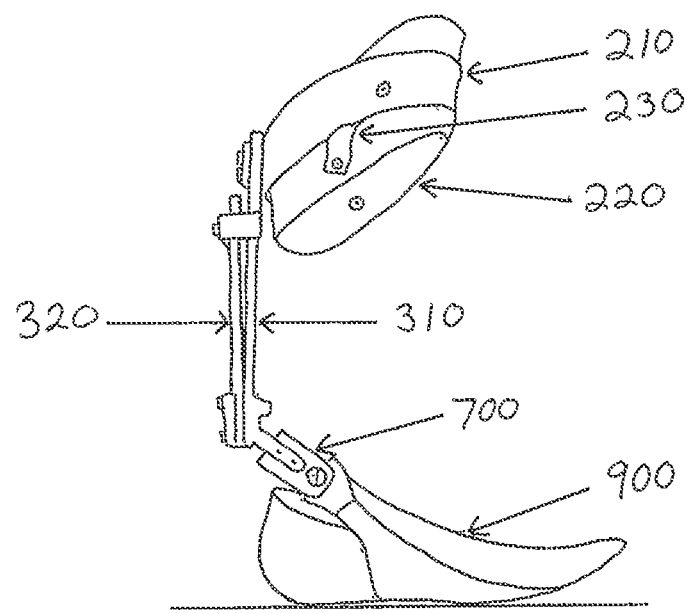

FIG. 2C depicts the early part of the "mid-stance" phase according to an embodiment of the invention which starts the second rocker or ankle rocker. As depicted, with the entire footplate 900 remaining in contact with the ground, the tibia continues to advance allowing the ankle to dorsiflex about 10 degrees. The ankle will return to close to neutral which will cause the mechanical ankle joint 700 to hit the "stop" mechanism. In the embodiment depicted, the superior channel of the joint has a pin installed to prevent further mechanical joint dorsiflexion and thus require posterior strut flexion for continued ankle joint dorsiflexion. As depicted, in the multiple strut system, the primary strut 310 is starting to flex, leaving the secondary strut 320 behind. Notably, as depicted, in this embodiment, the outer dynamic calf cuff component 210 is starting to slide inferiorly on the static calf cuff component 220. This can be noted on a patient by visually seeing the flexible straps 230 on the medial and lateral sides start to form a slight loop.

Figure 2D:
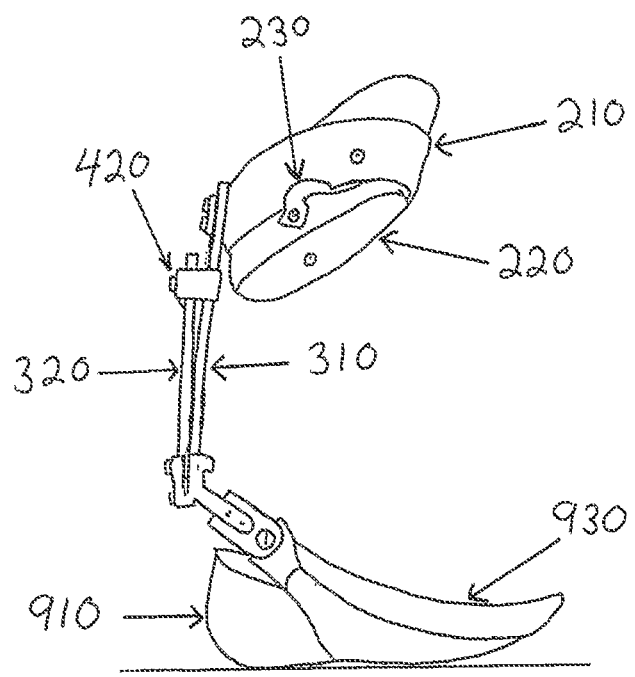

FIG. 2D depicts the later part of the "mid-stance" phase which continues the second (ankle) rocker. As depicted for this embodiment, the heel cup 910 and forefoot 930 still maintain contact with the ground and the tibia continues to advance, allowing about 5 more degrees of dorsiflexion. The primary strut 310 has continued to flex which has also caused the strut engager nut 420 to make contact with the secondary strut 320 which is forced to flex as well, increasing the resistance. Greater strut flexion is also creating greater inferior migration of the dynamic calf cuff component 210 over the static calf cuff component 220 as noted by increasing looping of the flexible straps 230.

Figure 2E:
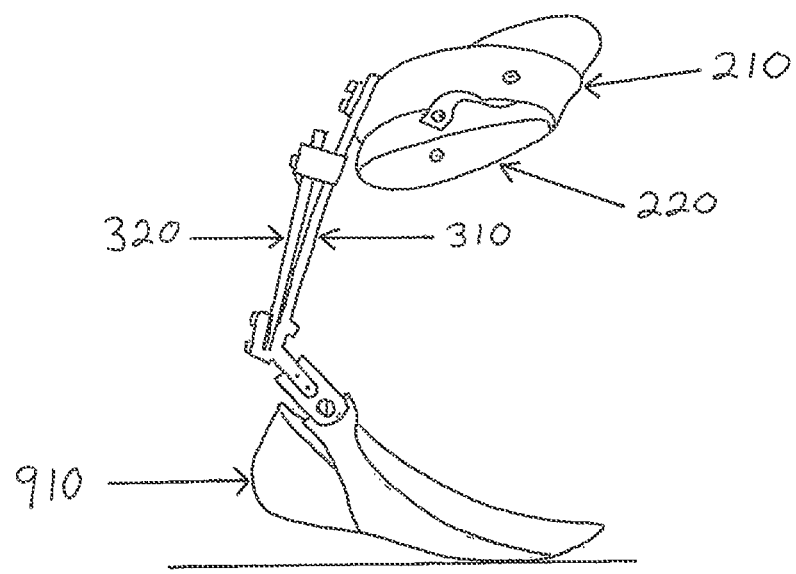

FIG. 2E depicts the "terminal stance" phase which includes the third and final rocker known as the forefoot rocker. As the tibia continues to advance with about 5 more degrees of dorsiflexion, greater resistance to dorsiflexion is created by the flexion of the primary 310 and secondary 320 struts causing the heel cup 910 to rise from the floor and subsequent forefoot rocker. More migration may be noted by the outer dynamic calf cuff component 210 over the inner static calf cuff component 220.

Figure 2F:
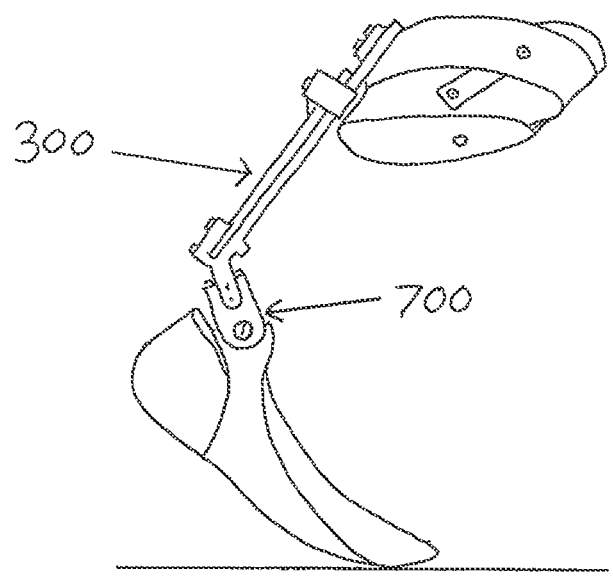

FIG. 2F depicts the "pre-swing" phase of gait. In this phase, the limb is starting to unload its weight-bearing cycle which causes the struts 300 to want to return to their original, non-flexed position by releasing the stored energy from the flexed position and transferring momentum rotationally to plantarflex the joint 700 and prepare the limb for advancement in swing.

Proximal Cuff

Referring to FIG. 1 and FIGS. 5A-5D, in a particular embodiment, the device of the instant invention 100 comprises a proximal cuff ("cuff") 200 which secures the device 100 to the leg of the wearer. In a particular embodiment, the cuff 200 is secured to the calf of the wearer. In another embodiment, the cuff 200 is attached at the proximal-anterior end of the primary posterior dynamic strut 310 which extends inferiorly to attach to an ankle joint 700 of the device 100. In contrast to prior art orthotic devices which comprise static, monolithic, one-piece, solid configurations strapped to the wearer, it is contemplated herein that the design of the proximal cuff 200 of the instant invention is such that a device 100 of the instant invention may be secured to the wearer with minimal conventional strapping.

As contemplated herein, in a particular embodiment depicted in FIG. 1 and FIGS. 5A-5D, the cuff 200 of the device of the instant invention 100 comprises both static 220 and dynamic 210 cuff components which can provide not only a comfortable and secure fit between the device 100 and the posterior calf and anterior shin of the wearer, but also can provide a degree of flexibility compatible with the dynamic nature of the AFO of the instant invention.

As depicted in FIG. 1 and FIGS. 5A-5D, in a particular embodiment, the cuff 200 comprises an inner static calf cuff component 220 and an outer dynamic calf cuff component 210. As depicted, the cuff 200 may be affixed at the proximal end of the primary posterior strut 310, e.g., by bolting or screwing the posterior of the outer dynamic cuff component 210 to the anterior face of the primary posterior dynamic strut. 310. In a particular embodiment, as depicted in FIG. 1, the dynamic calf cuff 210 may be connected to the primary strut 310 by two screws 215.

One or both cuff components may extend about the entirety of the circumference of the wearer's leg, or a portion thereof. In a particular embodiment, the inner static cuff component may comprise an anterior portion that fits snuggly against the shin of the wearer, without a corresponding posterior portion which fits against the triceps surae.

In a particular embodiment, the outer dynamic calf cuff component 210 and the inner static calf cuff component 220 are connected such that when one or more of the posterior struts 300 are engaged while the patient ambulates or runs in the device, the outer dynamic calf cuff component 210 can slide over the inner static calf cuff component 220 as the static calf cuff 220 stays with the patient's limb, securely affixed to the leg of the wearer while the dynamic calf cuff 210 migrates inferiorly and superiorly with strut flexion and extension. As such, the inner static calf cuff component 220 functions as a semi-rigid or rigid liner in the cuff 200. By allowing the dynamic calf cuff component 210 during strut engagement to migrate over the static calf cuff component 220 instead of the patient's skin, the design of the static/dynamic calf cuff 200 system provides the advantage of minimizing friction against the patient's skin, thus reducing small area pressure and/or shear stresses on the patient's skin that might result from posterior strut flexion and extension with concomitant calf cuff inferior/superior migration on the patient's limb.

As contemplated herein, in a particular embodiment, the static and dynamic calf cuff components are connected and move relative to each other by one or more straps, ties, or other apparatus that permit the dynamic calf cuff component to slidably translate over the inner static calf cuff component when the struts are engaged. As depicted in FIG. 1 and FIGS. 5A-5D, in a particular embodiment, the static calf cuff 220 is connected to the dynamic calf cuff 210 by flexible strapping 230 and rivets 235 on the medial and lateral side. In a particular embodiment, the apparatus may comprise one or more suspension straps 230 which suspend the inner, static calf cuff component 220 on the patient's limb when the struts 300 are unloaded yet still allows inferior migration of the outer dynamic calf cuff component 210 over the inner static calf cuff component 220 during strut 300 engagment.

In particular embodiments, the various components of the cuff system may be made of one or more commercially available materials including, but not limited to, webbings, elastics, carbon fiber or other materials that allow a dynamic response, co-polymers, thermoplastic materials, or other materials familiar to one of skill in the art of orthotics. Such materials include carbon fiber as well as composite materials such as combinations of carbon and graphite. In a particular embodiment, the outer dynamic cuff component may comprise carbon fiber. In one embodiment, the inner static calf cuff component may comprise a material selected from the group consisting of thermoplastics, carbon fiber, nylon or composites thereof. In a particular embodiment, the material is a copolymer of thermoplastic materials.

Similarly, in a particular embodiment, the apparatus that permits the dynamic calf cuff component to slidably translate over the inner static calf cuff component may be crafted out of a variety of materials suitable for the intended use, including, e.g., elastic or nonelastic fabric strapping. In a particular embodiment, the apparatus comprises suspension straps fabricated out of DACRON webbing.

Figure 6:
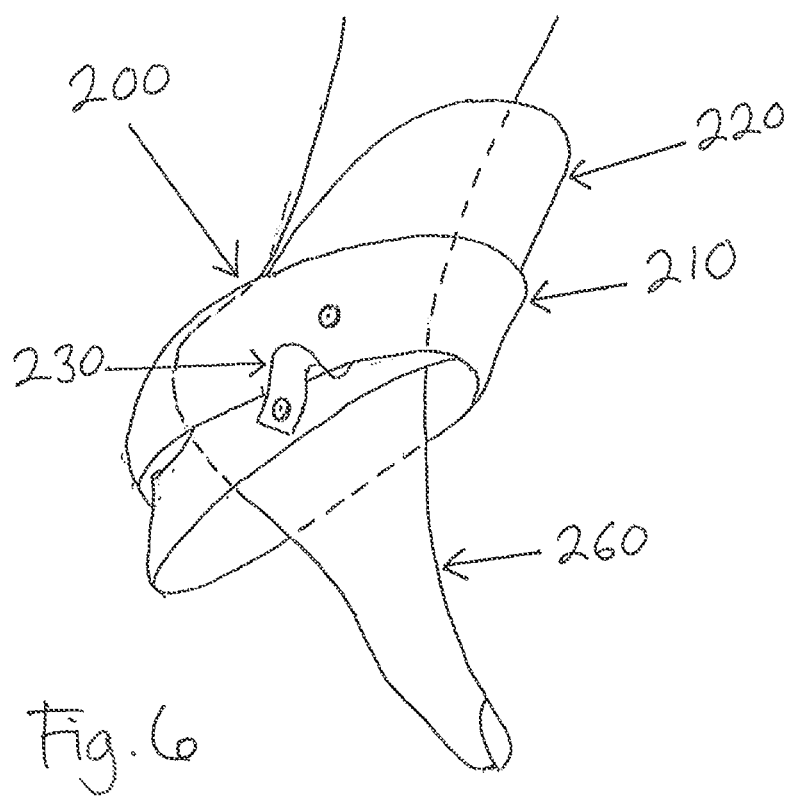
FIG. 6 illustrates a wearer's foot donning a proximal cuff according to an embodiment of the device of the instant invention (entire device not shown).

In a particular embodiment, as depicted in FIG. 6 and described in detail herein, the proximal cuff 200 is provided in a "step-through style" familiar to one in the field of orthotic devices, i.e., the patient dons the orthosis by placing a foot 260 through the cuff 200. It is contemplated herein, however, that a patient that cannot easily point the foot of an injured limb can don the inner static cuff component 220 first by sliding it superiorly relative to the dynamic cuff component 210, followed by the outer dynamic cuff component 210 which has a larger opening for the ankle.

As contemplated herein, in a particular embodiment, the size of the cuff of the instant device may be custom designed to ensure a secure fit, thus minimizing the need for the circumferential strapping commonly used on orthotic devices to secure the device to the wearer. Indeed, the outer dynamic and inner static calf cuffs work in conjunction to provide a strapless system for securing the device to the patient's limb. As depicted in FIGS. 5A-5D, in order to provide an appropriate fit and function of the cuff 200 of the device, the perpendicular distance between the point at the apex of the heel curve 240 and the apex on the dorsum side of the foot 250 of the patient is measured as indicated by the dotted line in FIG. 5A. The patient should plantarflex their foot 260 as tolerated while taking the measurement, as the plantarflexed posture closely represents the best position for donning the device. This measurement is utilized to determine the appropriate opening dimension from the anterior-distal trimline 270 to the posterior-superior trimline 275 of the inner static calf cuff and from the anterior-distal trimline 280 to the posterior-superior trimline 285 of the outer dynamic calf cuffs (FIGS. 5B and 5C). In a particular embodiment, the opening is greater than or equal to the measurement from the patient. The inner static calf cuff 220 (FIG. 5C) dimension can be greater than the actual measurement, but the outer dynamic calf cuff 210 dimension (in FIG. 5B) should closely approximate the actual measurement taken on the patient. The closer to the actual measurement, the less the posterior portion of the outer dynamic calf cuff 210 is angled inferiorly relative to the anterior portion of the calf cuffs 200 (FIG. 5D). This creates a better "lock" of the device on the patient's limb. In contrast, if the opening was turned into a smaller dimension, the patient would have difficulty donning the device since their foot wouldn't be able to pass through.

FIG. 6 depicts a contemplated donning method which allows the patient's foot 260 to pass through the opening of the outer dynamic calf cuff 210. In a particular embodiment, when the outer dynamic calf cuff 210 opening dimension is very close to the measured value on the patient, the anterior-distal portion of the inner static calf cuff 220 won't allow the foot 260 to pass through for donning when the calf cuff components 210, 220 are oriented in the operational positions. To allow the foot 260 to pass through, the patient can pull the inner static calf cuff 220 superiorly to increase the overall opening dimension. Once the foot 260 passes through, the inner static calf cuff 220 can be returned to its operational position creating the optimal "lock" with the patient's limb. Thus, the inner static calf cuff 220 not only can slide within the outer dynamic calf cuff 210 to make for easier donning, these cuff components 210, 220 can slide apart when the device is donned, thus increasing the surface area in the cuff 200 in contact with the calf and shin of the patient.

Given that the proximal cuff described herein can greatly reduce the amount of undesirable friction on the wearer's leg during use of the device, it is contemplated herein that a cuff of such design can be incorporated in a wide variety of orthotic devices in order to enhance the comfort and fit of such devices. Such devices include, but not limited to the style of the particular AFO described herein. Thus, in a particular aspect, the scope of the instant invention broadly includes an orthotic device comprising a proximal calf cuff comprising both inner static and outer dynamic cuff components such as described herein.

Dynamic Struts

As depicted in FIG. 1 and FIGS. 3A-3C, in one embodiment, the device of the instant invention 100 comprises a plurality of posterior dynamic struts 300, one or more of which may be employed ("engaged") in the device 100 during use to provide sufficient rigidity in the orthotic device 100 to support the wearer, not only while walking, but also while running or during other high impact activity. In a particular embodiment, the device 100 comprises at least a first posterior (primary) dynamic strut 310 which extends inferior and posterior to the tibia of the wearer (e.g., approximately vertically) and connects the proximal cuff 200 to distal ankle joints 700 in the device 100, and at least one second posterior (secondary) dynamic strut 320.

The length of the struts 300 in the device 100 may be customized as appropriate for each patient, and may be determined during fitting using conventional methods. Typically, the determined lengths of the posterior dynamic struts 300 for use in the orthotic device of the instant invention are relative to specific patient presentations such as tibia length and calf circumference. As depicted in FIG. 1 and FIGS. 3A-3C, it is understood herein that if the secondary posterior dynamic struts 320 are not affixed at their proximal end to the proximal cuff 200, in particular embodiments, the secondary posterior dynamic struts 320 for use in the device may be shorter than the primary strut 310 to not interfere with the mounting of the primary strut 310 to the proximal cuff 200.

The number of struts to be employed (engaged) during use of the device will depend on the level of support (rigidity) deemed necessary given the activity of the wearer; e.g., by engaging more than one posterior dynamic strut in the device, strut rigidity in the device may be increased to facilitate high impact activities such as running or jumping. It is contemplated herein that the wearer can manually adjust the posterior multiple strut engager during use such that the device may engage one or more struts. For example, the wearer can adjust the posterior multiple strut engager such that only the first posterior strut is engaged to provide sufficient support for walking; before running, the wearer may then adjust the posterior multiple strut engager such that two or more struts are engaged, thus producing a single strut structure ("assembly") of sufficient rigidity to support such higher impact activity.

Figure 11:
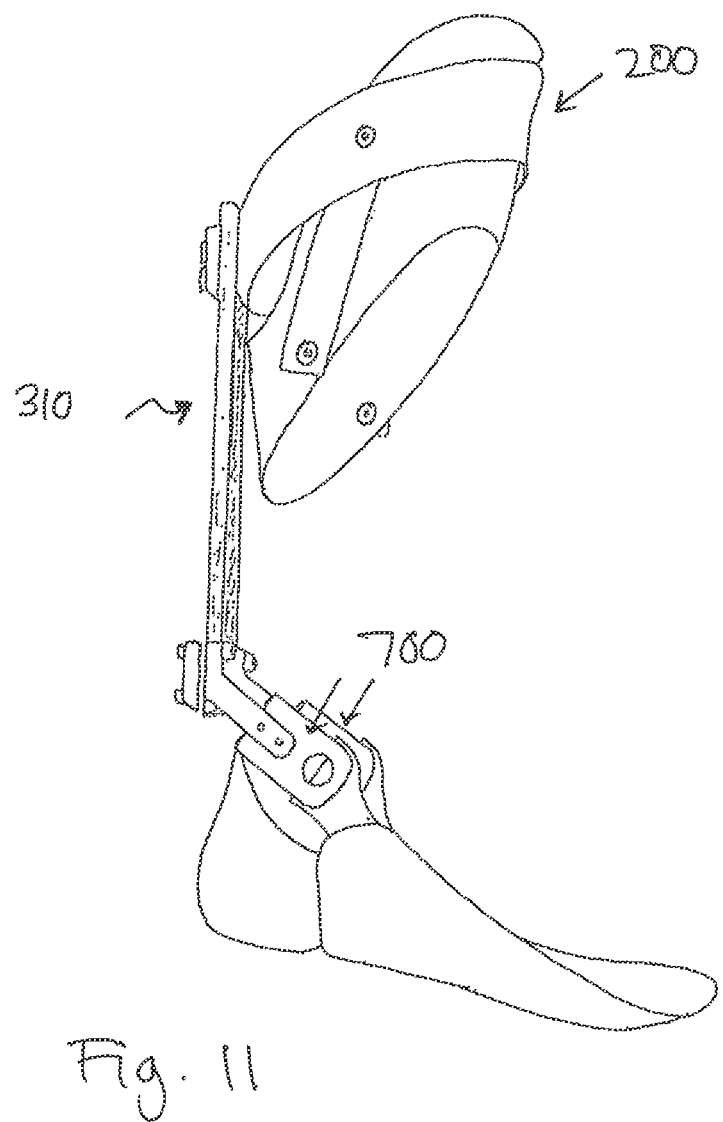
FIG. 11 depicts an orthotic device of the instant invention adjusted to form a single strut embodiment without a multiple strut engager or any additional posterior struts.

It is also contemplated herein that in situations wherein only a single posterior strut is required to provide sufficient support to the wearer, the device of the instant invention may be adjusted such that any additional posterior struts and the multiple strut engager are removed from the device, or not installed. Thus, the instant invention contemplates a single strut embodiment of the orthotic device. For example, when only the first posterior strut need be utilized for adequate patient function, the multiple strut engager and additional posterior struts can be removed or omitted from the device leaving a single strut embodiment, i.e., comprising only the primary posterior strut 310 attaching the proximal cuff 200 to distal ankle joints 700. See FIG. 11.

As explained in detail herein, more than one strut may be engaged in the device using a fastener such as, e.g., screws, clips, clamps, straps, springs, nuts, bolts and/or a combination thereof that may be manually adjusted to "stack" or "engage" a second strut in combination with a first strut "front to back", e.g., approximately vertically oriented, to form a strut assembly of greater rigidity than the first strut alone, and thus increase strut rigidity in the device and thus provide improved gait dynamics. It is contemplated herein that by stacking multiple struts and engaging the combined elastic features of the struts in this way, the struts in the device can mimic the elastic components of a calf muscle more closely than struts in prior art devices, e.g., posterior struts which are arranged side by side.

As depicted in FIGS. 2A-2F, it is contemplated herein that the use of dynamic multiple struts 300 in the instant invention allows some initial light flexion followed by exponential increase in strut resistance as the patient's tibia progresses in the gait cycle or as the patient increases their activity in jogging or running. In a sense, the multiple stage struts (i.e., struts that can flex at different intervals during the gait cycle) resemble the triceps surae activity transitioning from mid to late stance for regular walking, and a stretch-reflex in running. In essence, by creating tension in the overall device by engaging different struts at different times during the gait cycle, and providing energy storage and return, the device more closely mimics the natural function of the triceps surae muscles than other prior art AFOs.

Accordingly, it is contemplated herein that the dynamic struts of the device of the instant invention not only serve as a structural component of the device, but also as an energy storage and return component which permits dynamic controlled motion. As provided herein, the strut lever arm of the device of the instant invention extends superiorly from the ankle axis primarily parallel to the lower leg or tibia of the wearer. This strut system in line with the tibia acts as a second class lever in which the forces exerted by the patient's tibia and the resistive forces exerted by the strut are on the same side of the joint axis (ankle joint). Positioning the strut lever in this fashion (principal similar to a diving board) allows the use of a linearly modifiable lever to increase or decrease its mechanical advantage for the resistance of dorsiflexion torque created by the resultant ground reaction force anterior to the ankle joint axis. A longer strut lever arm provides greater resistance to dorsiflexion torque, and also provides greater energy storage and energy return for the patient as the dorsiflexion torque flexes the strut. The energy storage in the struts helps the wearer prepare for the next step by providing plantarflexion assist.

As one of skill in the art will appreciate, orienting the strut(s) approximately parallel and posterior to the tibia with an attachment of the distal end of the strut(s) to the joint requires the need for a dorsiflexion stop in the joint to initiate the strut resistance against the dorsiflexion torque (discussed below). Keeping the strut(s) approximately parallel to the tibia (i.e., approximately vertical) is also a patient care minded approach to keep the strut(s) close to the body which increases safety, e.g., when ambulating in adverse environments and/or wearing pants.

It is believed that the orientation of the lever arm and the lever arm classification of the instant invention is distinct from many conventional AFO devices which have a system that would be classified as a first class lever, i.e., the force exerted by the spring or elastomeric elements are on the opposite side of the joint axis from the force exerted by the resultant ground reaction force (principal similar to a seesaw). In such prior art devices, the lever arm is positioned perpendicular to the patient's tibia, thus requiring a posteriorly extended lever arm element from the heel to help increase the resistance created by the springs or elastic elements to counter the dorsiflexion torque and provide energy storage and return. In this system set up, if the posteriorly extended lever arm was positioned to be approximately parallel and posterior to the tibia, as the foot plantarflexed the lever arm would push into the posterior calf thus impeding free plantarflexion of the foot.

Struts of the device of the instant invention may be of any shape and dimensions (e.g., height and thickness) suitable for use in the orthotic device of the instant invention. In a particular embodiment, the struts may be crafted in a shape that facilitates vertically stacking or "piggybacking" of two or more struts together during engagement to form a strut assembly contained with the multistrut engager. For example, the struts may be flat and straight, or crafted to more closely contour the shape of the calf of the wearer, e.g., with a slightly concave anterior side and corresponding convex posterior side, and have anterior and posterior sides. To this end, in contrast to prior art orthotic devices which may comprise a plurality of posterior struts in a side by side configuration, the approximately vertical stacking or piggybacking of multiple posterior struts in the device of the instant invention provides that the posterior struts may be arranged "back to front", e.g., combining the posterior face of a first (primary) strut with the anterior face of a second posterior (secondary) strut. In another embodiment, a third posterior strut may be stacked with the first two struts by combining the posterior face of the secondary strut with the anterior face of a another secondary strut. In this manner, a plurality of posterior dynamic struts may be stacked approximately vertically in the orthotic device of the instant invention, i.e., arranged in an orientation from back to front in "piggyback" fashion.

One of skill in the art will appreciate that struts, outer calf cuff, and other components of the device of the instant invention can be manufactured out of any suitable material. As understood by one of skill in the art, a dynamic response can be characterized as comprising a bending deformation in response to a given force input. Materials that provide a dynamic response in an orthotic device include a variety of commercially available suitable materials. These include, but are not limited to, stainless steel, carbon, carbon fiber, titanium, fiberglass, resin, plastic, KEVLAR, aluminum, and composites thereof.

One of skill in the art will appreciate that by using conventional methods, the shape, dimensions, and material compositions of the struts may be customized to provide desired strut dynamics for the device of the instant invention; e.g., strut rigidity can be modified by designing the layup of carbon fiber during the lamination process of the entire orthosis according to conventional methods. In general, thinner struts made of carbon fiber can provide greater flexibility than thicker carbon fiber struts.

Multiple Dynamic Strut Engager

As discussed above, more than one posterior dynamic strut may be engaged in the orthotic device to increase the support provided by the device and thus provide the patient with improved motion. As contemplated herein, in a particular embodiment, the device of the instant invention comprises a plurality of posterior dynamic struts, one or more of which may be engaged in the device by the user depending on the intended gait of the user. It is contemplated herein that not only can the posterior dynamic struts in the device of the instant invention be used to simulate the triceps surae, but also the ability of the wearer to employ multiple struts in the device depending on gait impact level provides a more seamless kinesthetic response of the triceps surae than in conventional AFO devices. Indeed, the device of the instant invention provides an unexpected advantage by allowing the clinician and/or the patient to adjust the overall rigidity or resistance of the strut depending on the patient's comfort level and specific activity, i.e., a higher impact activity may require greater strut resistance, or greater resistance may be needed to prevent the patient from excessively dorsiflexing into a painful region within their foot and/or ankle. Thus, if the use of one strut in the device is found to be too flexible to provide support for the patient's movements, e.g., when the patient would want to run or engage in some other activity with a greater impact than walking, two or more struts may be used in conjunction to improve the support provided by the struts in the device.

It is contemplated herein that a user could manually adjust the strut engager such that the user can control when one or more secondary struts will bend along with the primary strut during the gait cycle. Thus, the user can control the timing when one or more additional struts would engage with the primary strut and thus provide additional strut rigidity in the device. In a particular embodiment discussed herein and depicted in FIGS. 3A-3C, a screw clamp 400 and a nut 420 may be used together as a strut engager. As contemplated herein, a secondary strut will engage sooner, or may engage as the same time as the primary strut, depending on the extent to which the screw and nut mechanism are adjusted. For example, the more the screw is tightened (see FIG. 3B), the sooner the secondary strut may engage and flex with the primary strut and provide additional rigidity; the looser the screw, the less likely the secondary strut will engage, or may not engage along with the primary strut at all (see FIG. 3C). The appropriate number of struts to support a particular gait may be determined by the wearer of the device without any undue experimentation. Thus, in a particular embodiment, a single durometer dynamic response strut which may be of sufficient rigidity to assist walking may be adjusted by the wearer to become a dual durometer dynamic response strut assembly which can provide sufficient additional support to assist a higher impact gait such as running.

In one embodiment, it is contemplated herein that the device may comprise one or more fasteners suitable for use as a "multiple dynamic strut engager." These fasteners can comprise a variety of mechanisms such as screws, clips, clamps, straps, springs, nuts, bolts or other devices and/or combinations thereof which can be used to engage one or more secondary struts in combination with the primary strut in the device. As depicted in FIG. 1 and FIGS. 3A-3C, in a particular embodiment, the multiple dynamic strut engager 400 may be affixed to the first posterior dynamic strut (primary strut) 310. It may be affixed to the first posterior dynamic strut using any suitable fasteners, including, e.g., materials selected from the group consisting of rivets, bolts, epoxy or a combination thereof. In one embodiment, the multiple dynamic strut engager can be a strap with a buckle for adjustability affixed to the posterior primary strut. Tightening the strap would mimic the same function as tightening the nut in the screw clamp/nut engager mechanism 400 depicted in FIG. 1 and FIGS. 3A-3C herein in order to engage the secondary strut sooner, while loosening the strap to create more slack would mimic loosening the nut to delay the engagement of the secondary strut.

As discussed above, as depicted in FIGS. 3A-3C, in a particular embodiment, the multiple dynamic strut engager 400 can be in the form of a screw clamp affixed to the posterior primary strut 310 (strut closest to the patient's leg). As depicted in FIGS. 3A-3C, a screw 410 is securely threaded into the posterior portion of the engager 400 and extends into the inside of the engager 400. On the inside of the engager 400 a nut 420 is threaded onto the screw 410. The nut 420 can be rotated on the screw 410 to change the location along the shaft of the screw 410. This enables the timing and amount of primary strut 310 flexion that can take place before the secondary strut 320 is engaged. The secondary strut 320 can have a small hole 340 in it at the level of the engager 400 (visible in FIG. 4D) and threaded screw 410 to allow it to pass through the threaded screw 410, but the nut 420 will impede any further passing.

For example, in an embodiment wherein the engager is a screw clamp such as depicted in FIG. 1, during fabrication, a first posterior dynamic strut 310 and a secondary posterior dynamic strut 320 may be passed through the screw clamp 400. The screw clamp 400 may be affixed to the posterior primary strut 310 e.g. using one or more rivets and epoxy. As contemplated herein, in this embodiment, when manually adjusted, the strut engager 400 causes one or more secondary posterior struts 320 to come into contact with the posterior primary strut 310 to form a strut assembly 330 with enhanced rigidity than the primary strut 310 alone. When increased rigidity of the struts is desired, the multiple dynamic strut engager 400 can be manually adjusted to "stack" or "engage" the second posterior dynamic strut in combination with the first posterior dynamic strut by screwing the clamp to form a strut assembly 330.

Ankle Joints

Figure 9:
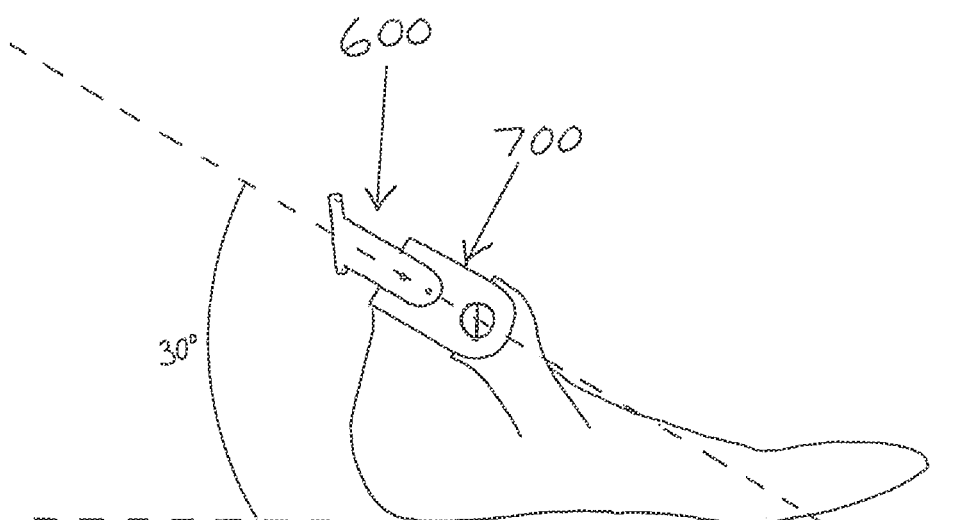
FIG. 9 depicts joints angled approximately 30 degrees in an embodiment of the device.

One of skill in the art can select the appropriate orthotic ankle joints ("joints") for use in the instant device based on the needs of the patient. As depicted in FIG. 9, in contrast to some prior art AFOs in which ankle joints are positioned straight up and down, in a particular embodiment of the instant invention, the joints 700 of the instant device are angled approximately 30 degrees from a straight line bisecting the base of the heel and the forefoot depending on specific patient presentation. Such measurements are familiar to one of skill in the art.

In a particular embodiment, the device of the instant invention may comprise two contoured double action ankle joints which are aligned with the anatomical talocrural joint of the wearer. In this embodiment of the instant invention, commercial contoured double action ankle joints with a 15 degree contour angle (Becker Orthopedics, Troy, MI) were angled posteriorly in this manner such that the device directs the contoured portion towards the midline of the patient's tibia in the sagittal plane allowing a bridging piece 600 (discussed below; see, e.g., FIG. 1, FIGS. 4A-4D, and FIG. 9) to be small and aesthetically pleasing. Angling the joints posteriorly also provides adequate length between the calf cuff and the bridging piece for fabrication of the dynamic struts. Contoured joints for use with the device of the instant invention may be created by one of skill in the art by modifying commercially available joints and/or by machining suitable materials (e.g., stainless steel or titanium) using conventional methods.

In addition, as understood by one of skill in the art of orthotics, during fabrication of the device, angle measurements may be taken "relative to the floor" according to conventional methods.

Figure 8:
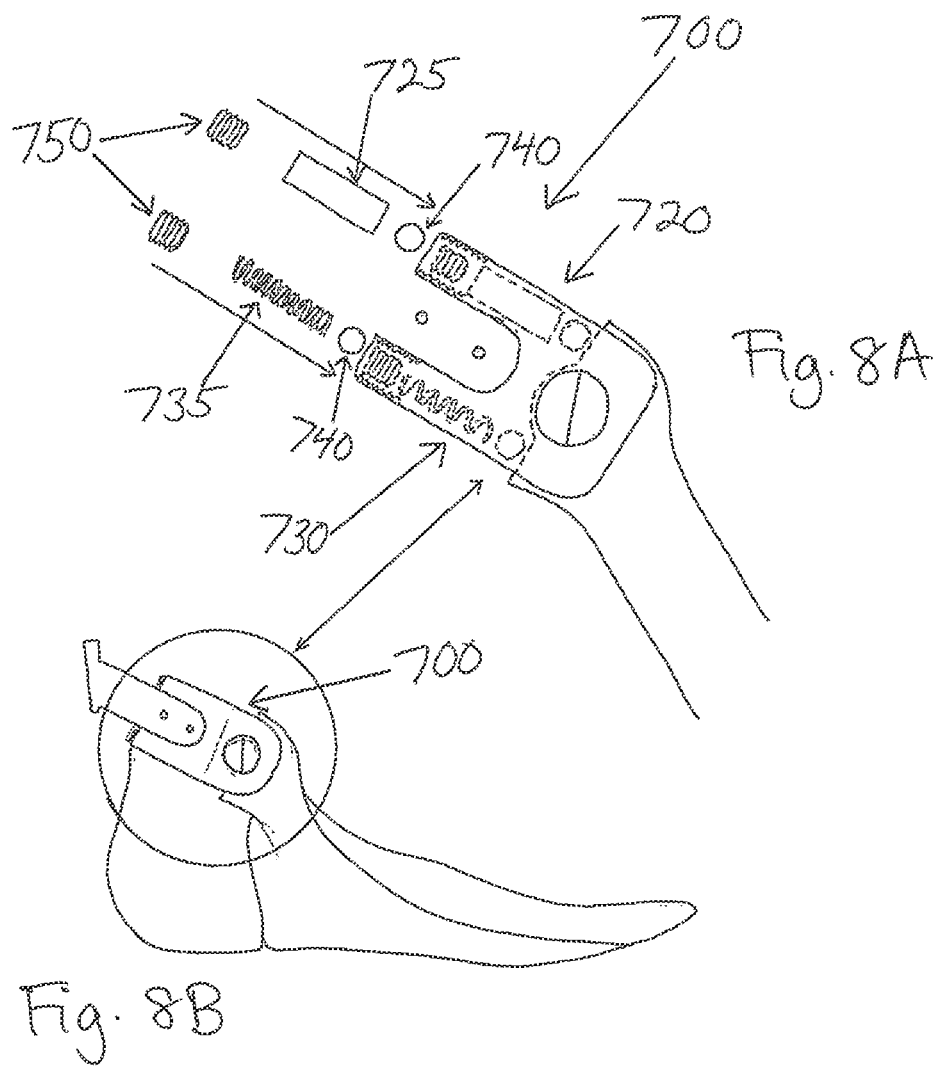
FIGS. 8A-8B depict an exploded view (FIG. 8A) and an assembled view (FIG. 88B) of a double action ankle joint for use in an embodiment of the instant invention.

As discussed above, in a particular embodiment, the device of the instant invention may comprise contoured double action ankle joints. The design and working mechanics of contoured double action ankle joints are familiar to one of skill in the art. For example, these particular joints typically have superior and inferior channels that run the length of the joint and are divided by an articulating axis. FIGS. 8A-8B provided herein depicts exploded and assembled views of a double action ankle joint for use in an embodiment of the instant invention. Such joint 700 comprises a superior channel 720 and an inferior channel 730. These channels provide several functions. The superior channel 720 can comprise a pin 725 which creates a dorsiflexion stop as the ankle moves into dorsiflexion by the tibia advancing. The stopping action is immediately followed by the engagement and flexing of the struts. The pin 725 within the superior channel 720 can be adjusted by the clinician and/or the wearer to properly time the engagement of the struts, e.g., to engage earlier or later in the stance phase. The pin 725 can be adjusted with a set screw to attain the desirable dorsiflexion angle according to conventional methods. In this embodiment, the working mechanism of the joint also comprises ball bearings 740 and screws 750 as depicted in FIGS. 8A-8B. Heel padding may need to be placed in the shoe if the plantarflexion angle is too much and causes a hyperextension moment at the patient's knee.

In particular embodiments, it is contemplated herein that for use in the device of the instant invention, the inferior channel can be left open or may include a spring to allow the desired plantarflexion of the ankle. In a particular embodiment depicted in FIGS. 8A-8B, the inferior channel 730 comprises a spring 735 which provides a controlled transition to foot flat in early stance and dorsi-assist in swing phase. This can also be adjusted by preloading the spring 735 or removing a spring and replacing it with a spring of greater or less rigid spring. The inferior channel 730 could also be left empty for patients with substantial anterior tibial muscle control to prevent uncontrolled plantarflexion during loading response in stance or dorsiflexion to prevent the toe from dragging on the ground in swing.

Although double action ankle joints may be used, it is contemplated herein that mechanical joints other than double action ankle joints may be used in the device of the instant invention, depending on the clinical needs of the patient. For example, if a patient does not require a device which can push the foot up, joints other than double action joints may be employed. Suitable joints include, but are not limited to, joints that comprise some form of dorsiflexion stop. Therefore, a joint that may only have one channel for placement of a pin may be used. One of skill in the art will appreciate that joints for use in the instant invention may be machined as needed, or may be obtained from a variety of commercial vendors.

Bridging Piece

As discussed above and depicted herein, e.g., in FIG. 1 and FIGS. 4A-4D, in a particular embodiment depicted, the orthotic device 100 may further comprise a bridging piece 600 for connecting the two modified joints 700 to the distal ends of the plurality of posterior dynamic strut(s) 300 posterior to the calf. In one embodiment, the bridging piece 600 comprises a removable central faceplate 610 and dual elongated side pieces 620 extending laterally from the faceplate 610. The side pieces can serve as attachment points for the joints 700 and the central faceplate 610 provides a mounting site for the posterior dynamic struts 300.

It is noted herein that the design of the bridging piece is such that a custom length measurement between the apices of the medial and lateral malleoli from individual patients may be incorporated into the bridging piece without affecting the fundamental design of the device of the instant invention. For example, typically, in particular embodiments, the bridging piece connected to the ankle joints provides a width between the two joints 10 mm greater than the width of the patient's ankle joint. This provides room for the ankle to move within the device of the instant invention without bumping up against the metal joint. For example, in a particular embodiment, if the patient's measurement between the apices of the malleoli is 7.5 cm then the bridging piece will be fabricated to create a distance of 8.5 cm between the mechanical joints. As discussed herein, the bridging piece also provides a mounting point for the dynamic strut(s). In one embodiment, the strut(s) may be mounted to the device by clamping the strut(s) in between the removable bridging piece central faceplate and the bridging piece using a plurality of screws. In a particular embodiment, four screws may be used to successfully mount the strut(s).

In a particular embodiment, in view of the approximately 30 degree position of the joint (and the built-in 15 degree angle of the commercial contoured joint), a posterior directed angle of approximately 8 degrees from perpendicular to the line bisecting the base of the patient's heel and forefoot was determined for the faceplate of the bridging piece by taking a rough angle measurement of a superior/inferior line connecting the calf belly to the Achilles tendon just superior to the level of the malleoli. It is understood herein that the angles employed in the device may be adjusted and customized depending on the physical dimensions and/or other needs of the patient. Thus, in particular embodiments, it is contemplated herein that the angle may range from about 25-35 degrees.

The bridging piece may be machined by one of skill in the art using various suitable materials, including but not limited to, titanium or steel. The bridging piece is fabricated from a rigid material to allow all intended flexion to take place in the struts. In a particular embodiment, the bridging piece may be manufactured using a 3D printer, and titanium. The resulting bridging piece may be used to bridge the two ankle joints together using rivets.

It is contemplated herein that to avoid decreasing the strength and structural integrity of the struts by drilling holes through the struts for mounting purposes, in a particular embodiment depicted in FIG. 1 and FIGS. 4A-4D, the distal end of the struts 300 may be secured to the device 100 by sandwiching the distal end of the struts 300 between the bridging piece 600 and the removable central faceplate of the bridging piece 610. A variety of fasteners may be used to secure the faceplate to the bridging piece, such as, e.g., bolts or rivets. For example, as depicted in FIGS. 4A-4D, in a particular embodiment, the device may comprise a plurality of bolts 510 screwed through the peripheries of the bridging piece 600 and the central faceplate of the bridging piece 610, thus avoiding the struts 300 (rather than protruding through the struts 300), in order to secure the struts 300 to the device. Additional components may be suitably fashioned and machined by one of skill in the art using conventional methods and employing conventional materials to secure the struts.

In a particular embodiment, a 30 degree angle of the joints not only provides room for installing a dynamic strut, but also allows stirrups to be directed distally and anteriorly into a footplate (discussed below) and to be contoured around the plantar surface of the user's foot posterior to the metatarsal heads for lamination. Contouring the stirrups to the foot which is achieved by bending and twisting the metal provides strength to the footplate and joint interface when the struts are loaded, and also less interference with shoe wear. As discussed herein, the angle of the joints may be modified as necessary by one of skill in the art using conventional methods given the physical dimensions of the patient.

Stirrups

Figure 10:
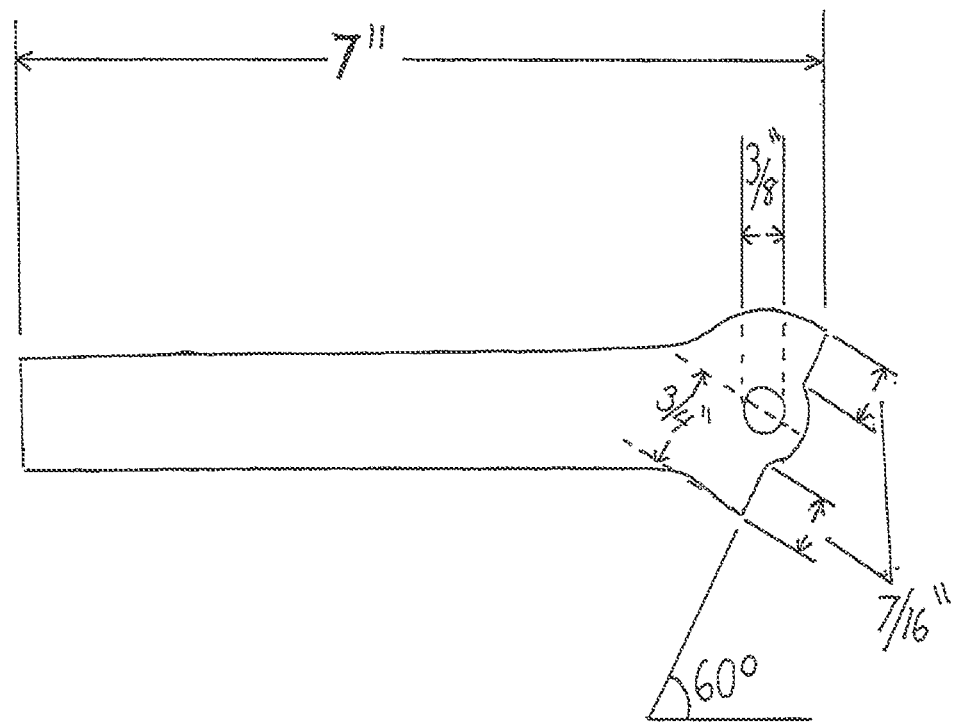
FIG. 10 depicts a schematic drawing with dimensions of a joint stirrup for use in an embodiment of the instant invention. As depicted, the joint stirrup may be about ⅛ inches thick and made of stainless steel.

The device may comprise joint stirrups to attach the joints to a footplate in the device. See, e.g. FIG. 10. Stirrups of this sort are familiar to one of skill in the orthotics field. In the manufacture of AFOs, stirrups may be inserted into the joint by sliding into slots in the joints, and the stirrups may be installed into the footplate by contouring and laminating, contouring and riveting, or both.

In a particular embodiment, as depicted in FIGS. 4A-4D, FIGS. 8A-8B, and FIG. 9 herein, contoured joints 700 are angled 30 degrees as discussed herein (e.g., see side view of joint 710), thus the contact surfaces of the head of the stirrups are also angled 30 degrees from perpendicular to the length of the stirrups 800. Advantages provided by this modification include: proper ankle range or motion; good surface contact for each channel of the ankle joint in the device; adequate adjustability to the channels without interfering with necessary ankle motion; and proper direction of the stirrup into the footplate to minimize shoe wear issues and appropriately distribute forces within the footplate to the joints. Commercially available stirrups (e.g., from Becker Orthopedics, Troy, MI) may be customized for use in the device of the instant invention, or otherwise machined from suitable materials (e.g., stainless steel ⅛ inches thick) by one of skill in the art using conventional methods. In an embodiment, the joint stirrups are contoured to fit the patient's foot anatomy and embedded within the lamination or thermoplastic in the footplate. The stirrups are connected to the contour ankle joints according to conventional methods.

Footplate

As depicted in FIG. 1, in a particular embodiment, the device 100 comprises a footplate 900 for supporting the foot of the wearer in the wearer's shoe which is worn with the device 100.

Figure 7:
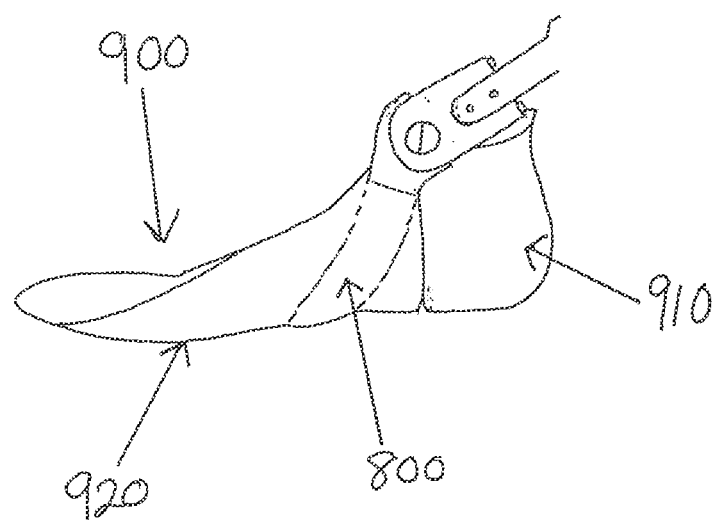
FIG. 7 depicts in dashed lines the distal ends of the distal double action joint stirrups 800 attached within and on the underside 920 of the distal footplate 900 in an embodiment of the device of the instant invention.

The footplate 900 may be fabricated in more than one section in order to enhance the overall flexibility of the footplate. In a particular embodiment depicted in FIG. 1, the footplate 900 can be designed and manufactured such that the section supporting the forefoot 930 (i.e., from the metatarsal heads to the toes) may be rigid or semi-rigid to allow some flexibility, depending on the patient's presentation. The footplate 900 may comprise the proximal ends of the stirrups 800. As depicted in FIG. 1 and FIG. 7, in a particular embodiment, the proximal ends of the stirrups 800 are embedded and laminated into the footplate 900 and contoured around the underside of the footplate 920 and plantar surface of the user's foot, in a section posterior to the metatarsal heads. In a particular embodiment, layers of carbon fiber and/or fabric for laminating and thermoset resin may be used to encompass the contoured stirrups.

The footplate for use with the device of the instant invention may be fabricated by one of skill in the art using conventional methods and commercially available materials. For example, the footplate can be laminated or made of thermoplastic or a combination of the two. For example, laminated components can be created with varying degrees of thickness, weight, rigidity, and may be rivetless; i.e., the stirrups are embedded in the structure. One of skill in the art will appreciate that thermoplastics may require greater relative thicknesses when compared to laminated components to achieve the same rigidity, and rivets or some form of fasteners can be used to attach additional pieces. As depicted in an embodiment of the invention in FIG. 1 and FIG. 7, a laminated footplate 900 may comprise the joint stirrups 800 (dashed line in FIG. 7) embedded within the lamination. As contemplated herein, in a particular embodiment depicted in FIG. 1 and FIG. 7, the footplate 900 may comprise a heel cup 910. In a particular embodiment, the heel cup 910 may be mounted to a rigid carbon fiber mid to forefoot portion of the footplate which comprises the embedded stirrups 800. In the embodiment depicted in the figures, for greater control, the heel cup 910 is designed to encompass the calcaneus of the wearer just inferior of the malleoli. This design provides the additional advantage of eliminating ROM interference with the joints since the joints are angled posteriorly. In particular embodiments, the heel portion of the footplate can be laminated in the same fashion as the rest of the footplate, or can be manufactured as a separate thermoplastic piece. In a particular embodiment, the heel cup comprises thermoplastic materials. It is contemplated herein that a thermoplastic heel cup would improve the fit of the device in the shoe of the wearer.

Although the invention herein has been described with reference to particular embodiments, it is to be understood that these embodiments, and any examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

What is claimed is:

1. An articulated dynamic ankle foot orthotic device comprising a plurality of posterior dynamic struts, an adjustable posterior multiple strut engager, a proximal cuff, distal mechanical ankle joints, and a distal footplate wherein the plurality of posterior dynamic struts comprises a first posterior dynamic strut and one or more additional posterior dynamic struts; wherein the adjustable posterior multiple strut engager is permanently fastened anteriorly to the proximal end of the first posterior dynamic strut; wherein said first posterior dynamic strut and one or more additional posterior dynamic struts are contained with the adjustable posterior multiple strut engager; wherein the plurality of posterior dynamic struts are each attached at a distal end to the distal mechanical ankle joints; wherein the first posterior dynamic strut is attached at a proximal end to the proximal cuff; wherein the distal mechanical ankle joints are attached medially and laterally to the distal footplate; and wherein the adjustable posterior multiple strut engager may be adjusted to engage said one or more additional posterior dynamic struts in combination with the first posterior dynamic strut, thereby stacking said one or more additional posterior dynamic struts in combination with the first posterior dynamic strut approximately vertically and forming a single posterior dynamic strut assembly of greater rigidity than the first posterior dynamic strut alone contained with the multiple strut engager and thus said one or more additional posterior dynamic struts engages at the same time as said first posterior dynamic strut or is adjusted such that said one or more additional posterior dynamic struts engages later than said first posterior dynamic strut.

2. The articulated dynamic ankle foot orthotic device of claim 1, wherein the proximal cuff comprises an inner static cuff component and an outer dynamic cuff component.

3. The articulated dynamic ankle foot orthotic device of claim 2, wherein the outer dynamic cuff component comprises a material that allows a dynamic response in the outer dynamic cuff.

4. The articulated dynamic ankle foot orthotic device of claim 3, wherein the material is selected from the group consisting of stainless steel, carbon, carbon fiber, titanium, fiberglass, resin, plastic, poly-para-phenylene terephthalamide, aluminum, and composites thereof.

5. The articulated dynamic ankle foot orthotic device of claim 4, wherein the material comprises carbon fiber.

6. The articulated dynamic ankle foot orthotic device of claim 2, wherein the inner static cuff component comprises a material selected from the group consisting of thermoplastics, carbon fiber, nylon or composites thereof.

7. The articulated dynamic ankle foot orthotic device of claim 6, wherein the material is a copolymer of thermoplastic materials.

8. The articulated dynamic ankle foot orthotic device of claim 2, wherein the outer dynamic cuff component is connected to the inner static cuff component such that the outer dynamic cuff component can slidably translate over the inner static cuff component during use.

9. The articulated dynamic ankle foot orthotic device of claim 1, further comprising a bridging piece, and wherein each of the plurality of posterior dynamic struts is attached at the distal end to the distal mechanical ankle joints via the bridging piece.

10. The articulated dynamic ankle foot orthotic device of claim 9, wherein the bridging piece is angled from about 0-15 degrees from a perpendicular line bisecting a line formed by bisecting a patient's base of heel and forefoot with respect to the patient's talocrural ankle axis.

11. The articulated dynamic ankle foot orthotic device of claim 10, wherein the bridging piece is angled about 8 degrees.

12. The articulated dynamic ankle foot orthotic device of claim 9, wherein each of the plurality of posterior dynamic struts are attached at the distal ends to the distal mechanical ankle joints by sandwiching said distal ends of said plurality of posterior dynamic struts between the bridging piece and a corresponding faceplate.

13. The articulated dynamic ankle foot orthotic device of claim 1, further comprising joint stirrups and wherein the distal mechanical ankle joints are attached to the distal footplate via the joint stirrups.

14. The articulated dynamic ankle foot orthotic device of claim 13, wherein the joint stirrups are angled from about 25-35 degrees with respect to a patient's talocrural ankle axis.

15. The articulated dynamic ankle foot orthotic device of claim 14, wherein the joint stirrups are angled about 30 degrees.

16. The articulated dynamic ankle foot orthotic device of claim 13, wherein the joint stirrups are double action joint stirrups.

17. The articulated dynamic ankle foot orthotic device of claim 1, wherein the distal mechanical ankle joints are angled from about 25-35 degrees from a straight line bisecting a patient's base of heel and forefoot with respect to the patient's talocrural ankle axis.

18. The articulated dynamic ankle foot orthotic device of claim 17, wherein the distal mechanical ankle joints are angled about 30 degrees.

19. The articulated dynamic ankle foot orthotic device of claim 1, wherein the distal footplate comprises a heel cup.

20. The articulated dynamic ankle foot orthotic device of claim 19, wherein the heel cup comprises a thermoplastic material.

21. The articulated dynamic ankle foot orthotic device of claim 1, wherein the plurality of posterior dynamic struts comprises a material selected from the group consisting of stainless steel, carbon, carbon fiber, titanium, fiberglass, resin, plastic, poly-para-phenylene terephthalamide, aluminum, and composites thereof.

22. The articulated dynamic ankle foot orthotic device of claim 21, wherein the material comprises carbon fiber.

23. The articulated dynamic ankle foot orthotic device of claim 1, wherein the adjustable posterior multiple strut engager comprises a fastener selected from the group consisting of screws, clips, clamps, straps, springs, nuts, bolts and a combination thereof.

24. The articulated dynamic ankle foot orthotic device of claim 23, wherein the fastener comprises a screw clamp and a nut and wherein the nut can be tightened or loosened to control the timing when the one or more additional posterior dynamic struts engages with the first posterior dynamic strut.

25. The articulated dynamic ankle foot orthotic device of claim 1, wherein the distal mechanical ankle joints are double action ankle joints.

26. The articulated dynamic ankle foot orthotic device of claim 25, wherein the double action ankle joints are contoured double action ankle joints.

27. The articulated dynamic ankle foot orthotic device of claim 1, wherein the adjustable posterior multiple strut engager comprises a fastener comprising a buckle and a strap, and wherein said strap may be tightened or loosened to control the timing when the one or more additional posterior dynamic struts engages with the first posterior dynamic strut.

28. A method of assisting a patient with a motor dysfunction of a lower limb comprising fitting the patient with the articulated dynamic ankle foot orthotic device of claim 1; placing the articulated dynamic ankle foot orthotic device on the lower limb of the patient; and adjusting the adjustable posterior multiple strut engager of the articulated dynamic ankle foot orthotic device such that at least one of the one or more additional posterior dynamic struts are combined with the first posterior dynamic strut, thereby forming a posterior dynamic strut assembly of greater rigidity than the first posterior dynamic strut alone, and thereby providing sufficient rigidity in the articulated dynamic ankle foot orthotic device to assist the patient with running or other high impact activity.

29. The method of claim 28, wherein one of said one or more additional posterior dynamic struts is combined with the first posterior dynamic strut.

30. The method of claim 28, wherein two or more of said one or more additional posterior dynamic struts are combined with the first posterior dynamic strut.

31. The method of claim 28, wherein the motor dysfunction is a functional deficiency due to triceps surae weakness.

32. The method of claim 28, wherein the adjustable posterior multiple strut engager is adjusted by the patient.

33. The method of claim 28, wherein the adjustable posterior multiple strut engager is adjusted by the patient during use, thereby providing a desired amount of strut rigidity in the device necessary for a desired gait.

34. A method of assisting a patient with a motor dysfunction of a lower limb comprising fitting the patient with the articulated dynamic ankle foot orthotic device of claim 1; placing the orthotic device on the lower limb of the patient; and adjusting the adjustable posterior multiple strut engager of the articulated dynamic ankle foot orthotic device such that only the first posterior dynamic strut is engaged in the articulated dynamic ankle foot orthotic device, thereby providing sufficient strut rigidity in the articulated dynamic ankle foot orthotic device to assist the patient with walking.

35. The method of claim 34, further comprising modifying the articulated dynamic ankle foot orthotic device to remove the adjustable posterior multiple strut engager and/or any additional posterior dynamic struts which are not engaged in the articulated dynamic ankle foot orthotic device.

36. The method of claim 34, wherein the motor dysfunction is a functional deficiency due to triceps surae weakness.

37. The method of claim 34, wherein the adjustable posterior multiple strut engager is adjusted by the patient.

38. The method of claim 34, wherein the adjustable posterior multiple strut engager is adjusted by the patient during use, thereby providing a desired amount of strut rigidity in the device necessary for a desired gait.

* * * * *